United States Patent
Yamazaki et al.

(10) Patent No.: US 11,591,631 B2
(45) Date of Patent: *Feb. 28, 2023

(54) GLUCOSE MONITORING METHOD AND GLUCOSE SENSOR

(71) Applicant: TOYOBO CO., LTD., Osaka (JP)

(72) Inventors: Yasuhiro Yamazaki, Tsuruga (JP); Atsushi Kawai, Tsuruga (JP); Takahide Kishimoto, Tsuruga (JP)

(73) Assignee: TOYOBO CO., LTD., Osaka (JP)

( * ) Notice: Subject to any disclaimer, the term of this patent is extended or adjusted under 35 U.S.C. 154(b) by 258 days.

This patent is subject to a terminal disclaimer.

(21) Appl. No.: 16/629,559

(22) PCT Filed: Jun. 22, 2018

(86) PCT No.: PCT/JP2018/023776
§ 371 (c)(1),
(2) Date: Jan. 8, 2020

(87) PCT Pub. No.: WO2019/017148
PCT Pub. Date: Jan. 24, 2019

(65) Prior Publication Data
US 2020/0172950 A1 Jun. 4, 2020

(30) Foreign Application Priority Data

Jul. 19, 2017 (JP) .............................. JP2017-140041
Aug. 4, 2017 (JP) .............................. JP2017-151687
Feb. 2, 2018 (JP) .............................. JP2018-017142

(51) Int. Cl.
*C12Q 1/32* (2006.01)
*C12Q 1/00* (2006.01)
*C12N 9/04* (2006.01)

(52) U.S. Cl.
CPC ........... *C12Q 1/006* (2013.01); *C12N 9/0006* (2013.01); *C12Q 1/32* (2013.01); *C12Y 101/9901* (2013.01)

(58) Field of Classification Search
CPC ............... C12N 9/0006; C12N 11/02; C12N 11/06–098; C12Y 101/9901; C12Q 1/001; C12Q 1/004–006; C12Q 1/32
See application file for complete search history.

(56) References Cited

U.S. PATENT DOCUMENTS

| | | | |
|---|---|---|---|
| 9,260,699 B2* | 2/2016 | Sumida | ............... C12N 9/0006 |
| 9,487,758 B2* | 11/2016 | Sumida | ................... C12Q 1/54 |
| 2011/0318810 A1 | 12/2011 | Tajima et al. | |
| 2014/0287478 A1 | 9/2014 | Sumida et al. | |
| 2014/0302542 A1 | 10/2014 | Araki et al. | |
| 2016/0319246 A1 | 11/2016 | Araki | |

FOREIGN PATENT DOCUMENTS

| | | |
|---|---|---|
| EP | 2719761 A1 | 4/2014 |
| EP | 3162893 A1 | 5/2017 |
| JP | 4648993 B2 | 3/2011 |
| JP | 2013-116102 A | 6/2013 |
| JP | 2015-084676 A | 5/2015 |
| JP | 2017-000137 A | 1/2017 |
| WO | 2013/065770 A1 | 5/2013 |

OTHER PUBLICATIONS

Piumi et al. "A novel glucose dehydrogenase from the white-rot fungus *Pycnoporus cinnabarinus*: production in Aspergillus niger and physicochemical characterization of the recombinant enzyme" Appl Microbiol Biotechnol, Dec. 2014;98(24):10105-18 (Year: 2014).*
GenCore Sequence Alignment of SEQ ID No. 5 of 16626559 and SEQ ID No. 1 of U.S. Pat. No. 9,260,699 (Year: 2022).*
Vashist et al., "Technology behind commercial devices for blood glucose monitoring in diabetes management: A review," *Anal. Chim. Act.*, 703(2): 124-136 (2011).
European Patent Office, Extended European Search Report in European Patent Application No. 18834325.5 (dated Mar. 9, 2021).
U.S. Food and Drug Administration, "Self-Monitoring Blood Glucose Test Systems for Over-the-Counter Use: Guidance for Industry and Food and Drug Administration Staff" (Oct. 11, 2016).
Japanese Patent Office, International Search Report in International Patent Application No. PCT/JP2018/023776 (dated Sep. 18, 2018).

* cited by examiner

*Primary Examiner* — Thane Underdahl
(74) *Attorney, Agent, or Firm* — Leydig, Voit & Mayer, Ltd.

(57) ABSTRACT

A glucose monitoring method and a glucose sensor, both of which use glucose dehydrogenase having a Michaelis constant (Km) for xylose of 600 mM or more and 3000 mM or less, and a Km for glucose of 0.1 mM or more and 100 mM or less, which provide for evaluating FADGDH in an aqueous system while reducing the practical influence of FADGDH on D-xylose.

17 Claims, 3 Drawing Sheets
Specification includes a Sequence Listing.

GLUCOSE MONITORING METHOD AND GLUCOSE SENSOR

CROSS-REFERENCE TO RELATED APPLICATIONS

This patent application is the U.S. national phase of International Patent Application No. PCT/JP2018/023776, filed on Jun. 22, 2018, which claims the benefit of Japanese Patent Application No. 2017-140041, filed on Jul. 19, 2017, Japanese Patent Application No. 2017-151687, filed on Aug. 4, 2017, and Japanese Patent Application No. 2018-017142, filed on Feb. 2, 2018, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 26,511 bytes ASCII (Text) file named "747103SequenceListing.txt," created Jan. 8, 2020.

TECHNICAL FIELD

The present invention relates to a glucose monitoring method and a glucose sensor.

BACKGROUND ART

Self-monitoring of blood glucose (SMBG) is important for diabetic patients themselves to measure, manage, and control their blood sugar levels on a daily basis for use in treatment. In recent years, simple self-monitoring blood glucose meters using an electrochemical biosensor have been widely used for SMBG. A typical biosensor of this type is, for example, a device in which electrodes and an enzyme reactive layer are formed on an insulating substrate.

Known glucose-monitoring enzymes used in biosensors include glucose dehydrogenase (hereinafter also referred to as "GDH") and glucose oxidase (hereinafter also referred to as "GO") (EC 1.1.3.4). Depending on the difference in the required coenzyme, GDH is further classified into pyrroloquinoline quinone-dependent glucose dehydrogenase (hereinafter also referred to as "PQQGDH") (EC 1.1.5.2 (formerly EC 1.1.99.17)) and flavin-binding glucose dehydrogenase (e.g., flavin adenine dinucleotide-dependent glucose dehydrogenase (hereinafter also referred to as "FADGDH") (EC 1.1.99.10)).

It has been pointed out that a glucose monitoring method using GO is easily affected by dissolved oxygen in the measurement sample, and that dissolved oxygen affects the measurement results. In contrast, it has been pointed out that a method using PQQGDH is not affected by dissolved oxygen, but acts on sugars other than glucose, such as maltose and lactose. Further, it is known that a method using FADGDH is not affected by dissolved oxygen, and barely acts on maltose or lactose.

In addition to maltose and lactose, D-xylose is also referred to as a sugar that causes problems for diabetes patients to measure their blood sugar levels. At a medical site, D-xylose is used for xylose absorption for evaluating the ability of carbohydrate absorption from the small intestine. Therefore, when a diabetic patient undergoes the test, if blood sugar levels are measured using glucose dehydrogenase having D-xylose activity, the accuracy of the measured values may be impaired.

In particular, regarding methods for evaluating the influence of contaminants in SMBG sensors, NPL 1 has been published by the US FDA. As for the influence of D-xylose, NPL 1 recommends that a response value is measured in a solution in which a glucose solution is spiked with D-xylose at a concentration of 200 mg/dL, and that the response value is shown with 95% confidence intervals with respect to a response value obtained under conditions without spiking.

Accordingly, D-xylose activity on SMBG sensors is often evaluated using the spike test. Moreover, in order to reliably ensure that there is no influence of D-xylose, performance evaluation may be conducted while setting the D-xylose concentration used in the spike test to higher than the concentration described in NPL 1.

Practical D-xylose activity in SMBG sensors is often evaluated using the spike test, as in NPL 1, whereas the D-xylose activity of FADGDH used in SMBG sensors is currently often discussed mainly in terms of activity on D-xylose in aqueous systems. For example, PTL 1 indicates that the amount of D-glucose can be accurately measured by using FADGDH having a D-xylose activity of 2% or less when activity on D-glucose is 100%.

CITATION LIST

Patent Literature

PTL 1: JP4648993B

Non-Patent Literature

NPL 1: Self-Monitoring Blood Glucose Test Systems for Over-the-Counter Use: Guidance for Industry and Food and Drug Administration Staff, published on Oct. 11, 2016 (http://www.raps.org/Regulatory-Focus/News/2016/10/07/25966/FDA-Finalizes-Two-Guidance-Documents-on-Blood-Glucose-Monitoring-Systems/)

SUMMARY OF INVENTION

Technical Problem

As described above, the evaluation of the D-xylose activity of FADGDH used in SMBG sensors has been discussed mainly in terms of activity on D-xylose in aqueous systems, and there are many reports on FADGDH, which is said to have low activity on D-xylose, based on this evaluation method. However, there is a problem that FADGDH, which has low activity on D-xylose in aqueous systems, is not necessarily unaffected by xylose in sensor systems. In fact, regarding whether evaluation methods in aqueous systems actually reflect activity on D-xylose in glucose sensors represented by SMBG sensors, GDH physicochemical characteristics reflecting that there is no practical influence on D-xylose on glucose sensors have not been reported so far, other than simply comparing reactivity for each substrate.

An object of the present invention is to find GDH physicochemical characteristics reflecting that there is no practical influence on D-xylose on glucose sensors, which have not been clarified so far. More specifically, an object of the present invention is to provide a glucose sensor and a glucose monitoring method, wherein a method for evaluating GDH in an aqueous system, the method reflecting the activity of GDH on D-xylose on a glucose sensor, is constructed to reduce the practical influence thereof on D-xylose.

Solution to Problem

As a result of extensive research in consideration of the above objects, the present inventors found that, as physicochemical characteristics satisfying that GDH has no influence on D-xylose when applied to a glucose sensor, it is important that the Michaelis constant (hereinafter also referred to as "Km") of GDH for D-glucose is 100 mM or less, and that the Michaelis constant of GDH for D-xylose is 600 mM or more. The present inventors also found that a glucose sensor that is practically not affected by D-xylose can be produced by using GDH having the above characteristics. Thus, the present invention has been completed.

Specifically, the inventions represented by the following are provided.

Item 1.

A glucose monitoring method using glucose dehydrogenase comprising the following properties (1) and (2):

(1) a Km for D-glucose of 0.1 mM or more and 100 mM or less; and (2) a Km for D-xylose of 600 mM or more and 3000 mM or less.

Item 2.

The glucose monitoring method according to Item 1, wherein the glucose dehydrogenase has a Km for D-xylose of 619 mM or more and 3000 mM or less.

Item 3.

The glucose monitoring method according to Item 1, wherein the glucose dehydrogenase has a Km for D-xylose of 736 mM or more and 3000 mM or less.

Item 4.

The glucose monitoring method according to any one of Items 1 to 3, wherein an enzyme electrode comprising glucose dehydrogenase is used.

Item 5.

The glucose monitoring method according to any one of Items 1 to 4, wherein the glucose dehydrogenase further has a D-xylose activity of 95% or more and 105% or less in an enzyme electrode method, where the D-xylose activity is a ratio (%) of a response value to a solution in which a 10 mM D-glucose solution is spiked with 20 mM D-xylose, with respect to a response value to a 10 mM glucose solution.

Item 6.

A glucose sensor comprising glucose dehydrogenase on a carbon electrode or a metal electrode, the glucose dehydrogenase comprising the following properties (1) and (2):

(1) a Km for D-glucose of 0.1 mM or more and 100 mM or less; and (2) a Km for D-xylose of 600 mM or more and 3000 mM or less.

Item 7.

The glucose sensor according to Item 6, wherein the glucose dehydrogenase further has a D-xylose activity of 95% or more and 105% or less in an enzyme electrode method, where the D-xylose activity is a ratio (%) of a response value to a solution in which a 10 mM D-glucose solution is spiked with 20 mM D-xylose, with respect to a response value to a 10 mM glucose solution.

Item 8.

The glucose sensor according to Item 6 or 7, further comprising a mediator on the carbon electrode or metal electrode.

Item 9.

A method for producing a glucose sensor, comprising measuring the Michaelis constant (Km) of glucose dehydrogenase for xylose.

Item 10.

The method for producing a sensor according to Item 9, further comprising measuring the Km of glucose dehydrogenase for xylose, and selecting glucose dehydrogenase having a Km of 600 mM or more.

Advantageous Effects of Invention

The present invention makes it possible to provide a glucose monitoring method and a glucose monitoring sensor, both of which can accurately measure blood sugar levels without being affected by D-xylose.

DESCRIPTION OF EMBODIMENTS

Figure 1:
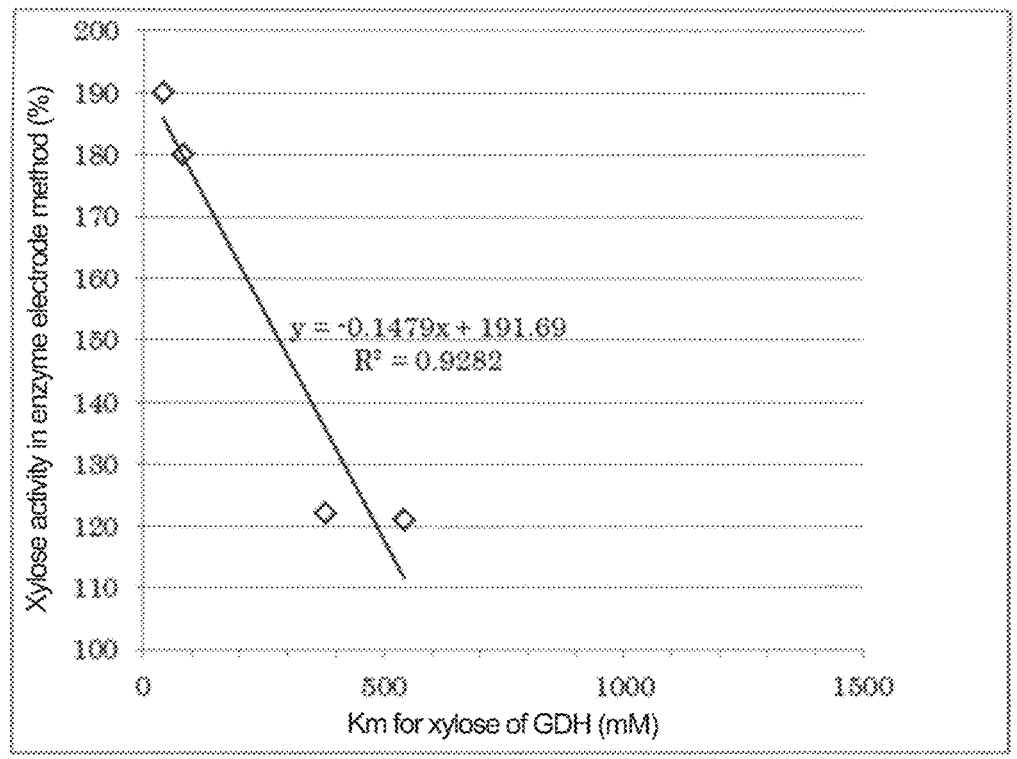
FIG. 1: A graph showing the Michaelis constant (Km) for D-xylose of GDH1 to GDH4, and D-xylose activity in an enzyme electrode method, in Example 1.

The present invention is described in detail below.

One aspect of the present invention is a method for measuring D-glucose by an enzyme electrode method using glucose dehydrogenase having a Michaelis constant (Km) for D-xylose of 600 mM or more.

The glucose monitoring method of the present invention is characterized by using glucose dehydrogenase that catalyzes the following reaction:

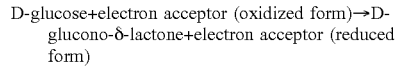

The glucose dehydrogenase used in the present invention is not particularly limited, but is preferably flavin-binding glucose dehydrogenase. Flavin is a group of derivatives having a substituent at position 10 of dimethylisoalloxazine, and is not particularly limited as long as it is an enzyme that uses a flavin molecular species as a coenzyme. Examples of flavin compounds include flavin adenine dinucleotide (FAD), flavin adenine mononucleotide (FMN), and the like; FAD is particularly preferable.

The glucose dehydrogenase used in the present invention is characterized by having a sufficiently high affinity for D-glucose and a sufficiently low affinity for D-xylose. More specifically, as the affinity for D-glucose, Km for D-glucose is 100 mM or less, and as the affinity for D-xylose, Km for D-xylose is 600 mM or more. The properties other than Km for D-glucose and Km for D-xylose are not particularly limited. For example, Km for D-glucose may be 100 mM or less, and more preferably 90 mM or less. Since it is important that Km for D-glucose is low, the lower limit thereof is not particularly limited, but is greater than 0.1 mM, preferably 1 mM or more, more preferably 5 mM or more, and even more preferably 10 mM or more. Km for D-xylose may be 600 mM or more, preferably 619 mM or more, more preferably 650 mM or more, 700 mM or more, 736 mM or more, 750 mM or more, or 819 mM or more, and particularly preferably 850 mM or more. Since it is important that Km for D-xylose is high, the upper limit thereof is not particularly limited; however, as estimated from the solubility of D-xylose, the upper limit of Km is preferably 3 M or less, more preferably 2.5 M or less, 2 M or less, or 1.5 M or less, and particularly preferably 1.3 M or less.

Other properties of the glucose dehydrogenase used in the present invention are not particularly limited. For example, the optimum temperature is preferably 35° C. to 65° C., more preferably 40° C. to 60° C., and even more preferably 45° C. to 55° C.

Regarding temperature stability, the residual activity after treatment at 50° C. for 15 minutes is preferably 70% or more, more preferably 75% or more, and even more preferably 80% or more.

The optimum pH is preferably 5.0 to 8.5, more preferably 5.5 to 8.0, and even more preferably 6.0 to 7.5.

The pH stability is preferably 2.5 to 10.0, more preferably 3.5 to 9.0, and even more preferably 4.5 to 8.0, under treatment conditions at 25° C. for 16 hours.

The sugar content is preferably 5% to 50%, more preferably 10% to 40%, and even more preferably 20% to 30%.

In particular, preferable glucose dehydrogenase has the following properties as basic properties, in addition to Km for D-xylose.
Optimal temperature: 50 to 55° C.
Temperature stability: residual activity after treatment at 50° C. for 15 minutes is 80% or more
Optimum pH: around 7.0
pH stability: 4.0 to 8.0 (25° C., 16 hours)
Sugar content: 20 to 50%
Km for D-glucose: 50 to 70 mM Alternatively, glucose dehydrogenase having the following properties may be used.
Optimal temperature: 50 to 70° C.
Temperature stability: residual activity after treatment at 50° C. for 15 minutes is 80% or more
Optimum pH: 6.5 to 7.5
pH stability: 2.5 to 10.0 (25° C., 16 hours)
Sugar content: 10 to 40%
Km for D-glucose: 10 to 90 mM Alternatively, glucose dehydrogenase having the following properties may be used.
Optimal temperature: 45 to 50° C.
Temperature stability: residual activity after treatment for 15 minutes at 45° C. is 80% or more
Optimal pH: 6.0 to 6.5
pH stability: 3.5 to 6.5 (25° C., 16 hours)
Sugar content: 20 to 50%
Km for D-glucose: 5 to 20 mM The origin of the glucose dehydrogenase used in the present invention is not particularly limited. Examples include fungi, such as the genera *Penicillium, Aspergillus,* and *Talaromyces*; and microorganisms classified into the Mucoraceae, such as the genera *Mucor, Absidia,* and *Actinomucor.*

Examples of the genus *Penicillium* include species such as *Penicillium italicum* and *Penicillium lilacinoechinulatum.* Examples of the genus *Aspergillus* include species such as *Aspergillus oryzae, Aspergillus terreus, Aspergillus niger,* and *Aspergillus flavus.* Further, examples of microorganisms classified into the Mucoraceae include the genera *Mucor, Actinomucor, Rhizoh Mucor, Circinella, Parasitella, Zygorhynchus, Dicranophora, Spinellus, Sporodiniella, Rhyzopus, Absidia, Chlamidoabsidia,* and *Thermomucor.* Examples of the genus *Mucor* include species such as *Mucor guilliermondii, Mucor prainii, Mucor javanicus, Mucor hiemalis,* and *Mucor circinelloides.*

The glucose dehydrogenase used in the present invention may be obtained by extracting and purifying a natural source. If information, such as the amino acid sequence thereof and the gene sequence encoding the amino acid sequence, is already known (e.g., the amino acid sequence of SEQ ID No. 5), glucose dehydrogenase may be produced by a genetic engineering technique based on such information. The glucose dehydrogenase used in the present invention may be a naturally occurring enzyme, or a product obtained by altering or chemically modifying the amino acid sequence of a naturally occurring enzyme by a known genetic engineering technique (hereinafter, also referred to as a "variant").

As long as it is glucose dehydrogenase having a Michaelis constant for D-xylose of 600 mM or more, preferable examples of the variant include glucose dehydrogenase having 70% or more (preferably 80% or more, more preferably 90% or more, even more preferably 95% or more, still more preferably 98% or more, and further still more preferably 99% or more) identity with the amino acid sequence represented by SEQ ID No. 5. Further, as long as it is glucose dehydrogenase having a Michaelis constant for D-xylose of 619 mM or more, a preferable example of the variant may be one comprising an amino acid sequence with substitution, deletion, insertion, and/or addition of one or more amino acid residues in the amino acid sequence represented by SEQ ID No. 5.

One aspect of the glucose monitoring method of the present invention has the following property (I) and/or (II).
(I) D-glucose is measured by an enzyme electrode method using glucose dehydrogenase having a Michael is constant (Km) for D-xylose of 619 mM or more.
(II) D-xylose activity (ratio (%) of a response value to a solution in which a 10 mM D-glucose solution is spiked with 20 mM D-xylose, with respect to a response value to a 10 mM D-glucose solution) in an enzyme electrode method is 80% or more and 120% or less, preferably 85% or more and 115% or less, more preferably 90% or more and 110% or less, even more preferably 95% or more and 105% or less, and still more preferably 97% or more and 103% or less.

In contrast, it was found that "activity on D-xylose in an aqueous system," which has been used as an evaluation criterion for substrate specificity in glucose measurement, was actually not correlated with "D-xylose activity in an enzyme electrode method." The reason for this result is considered to be that the D-xylose activity of FADGDH on D-glucose has been expressed only by activity at any one substrate concentration in an aqueous system. For example, the D-xylose activity of FADGDH derived from *Mucor prainii* described in PTL 1 was 1.4%, which was acquired at 50 mM, according to the Examples of PTL 1. However, according to the inventors' investigation, when the substrate concentration used for measurement was changed to 200 mM, activity on 200 mM D-xylose was 3.6% in an aqueous system, when activity on 200 mM D-glucose was set to 100%. This result shows that the "activity on D-xylose in an aqueous system" is an index dependent on the concentration of the substrate to be measured.

The glucose sensor of the present invention is characterized by using glucose dehydrogenase having a Michaelis constant (Km) for D-xylose of 600 mM or more and 3000 mM or less, and a Km for D-glucose of 0.1 mM or more and 100 mM or less.

The glucose sensor of the present invention is not particularly limited, and examples include the SMBG sensors described above. The glucose sensor may also be equipped with an arithmetic unit for calculating a blood sugar level based on the signal intensity obtained from a response to glucose, and a display for showing the calculated blood sugar level. In addition, the glucose sensor of the present invention may be a sensor onto a reactive layer of which blood or a diluted solution of blood as an analyte is allowed to fall in drops, or the sensor may be equipped with a needle for perforating the skin of a subject to collect blood and/or a flow path for delivering blood; the needle and/or flow path may be attachable. Alternatively, the sensor may be a sensor for use in CGM (continuous glucose monitoring), which can continuously monitor blood sugar levels, or FGM (flash glucose monitoring).

In the present invention, the D-glucose concentration can be measured as follows, for example. That is, a sample containing D-glucose is added to the reactive layer connected to electrodes on the glucose sensor to cause a reaction, followed by the application of a constant voltage across the electrodes. The current is monitored, and the current accumulated during a predetermined time period from the start of voltage application is summed, or the current value after a predetermined time period is passed from the start of voltage application is measured. The D-glucose concentration of the sample can be calculated from the value on the basis of a calibration curve prepared from a D-glucose solution of standard concentration.

1. Glucose Dehydrogenase Activity Measurement Method

In the present invention, the activity of glucose dehydrogenase is defined using, as 1 unit (U), the amount of enzyme that reduces 1 micromole of DCPIP per minute in the presence of a substrate according to a method using a reagent having the following formulation.

Reagent 50 mM PIPES buffer (pH: 6.5; containing 0.1% TritonX-100)

24 mM PMS solution 2 mM 2,5-dichlorophenolindophenol (DCPIP) solution

1 M D-glucose solution

The above solutions are mixed to prepare a reaction reagent comprising 200 mM D-glucose, 0.068 mM DCPIP, 1.63 mM PMS, 0.1% Triton X-100, and 35 mM PIPES buffer (pH 6.5).

Measurement Conditions

First, 3 ml of reaction reagent is pre-warmed at 37° C. for 5 minutes. 0.1 ml of GDH solution is added thereto, and the resulting mixture is gently mixed. Then, the change in absorbance at 600 nm is record for 5 minutes by a spectrophotometer adjusted at 37° C. with water as a control, and the change in absorbance per minute ($\Delta OD_{TEST}$) is measured from the straight line portion. In a blind test, a solvent that dissolves GDH is added to the reagent mixture, instead of the GDH solution, and the change in absorbance per minute ($\Delta OD_{BLANK}$) is similarly measured. From these values, GDH activity is determined according to the following formula. One unit (U) in GDH activity is defined as the amount of enzyme that reduces 1 micromole of DCPIP per minute in the presence of D-glucose at a concentration of 200 mM.

$$\text{Activity (U/ml)} = \{-(\Delta OD_{TEST} - \Delta OD_{BLANK}) \times 3.0 \times \text{dilution magnification}\} / \{16.3 \times 0.1 \times 1.0\}$$

In the formula, 3.0 is the volume (ml) of the reaction reagent and the enzyme solution, 16.3 is the millimolar molecular extinction coefficient ($cm^2$/micromole) under the conditions for this activity measurement, 0.1 is the volume (ml) of the enzyme solution, and 1.0 is the optical path length (cm) of the cell.

2. Michael is Constant for D-Glucose of Glucose Dehydrogenase

The Michaelis constant (Km) for D-glucose of glucose dehydrogenase is calculated from the Lineweaver-Burk plot in the present invention. Specifically, it can be calculated by measuring the reaction rate at four D-glucose concentrations (30 mM, 50 mM, 100 mM, and 200 mM) in the D-glucose dehydrogenase activity measurement method described in 1 above.

3. Method for Evaluating D-Xylose Activity Glucose Dehydrogenase in Aqueous System The D-xylose activity of glucose dehydrogenase in an aqueous system is evaluated as follows. In the glucose dehydrogenase activity measurement method described in 1 above, the reactivity for glucose and the reactivity for D-xylose are obtained by two methods with two substrate concentrations set to 50 mM and 200 mM, and the ratio of the reactivity for xylose to the reactivity for glucose is calculated for evaluation. The reactivity for xylose is obtained under the following measurement conditions.

Reagent 50 mM PIPES buffer (pH: 6.5; containing 0.1% TritonX-100)

24 mM PMS solution 2 mM 2,5-dichlorophenolindophenol (DCPIP) solution

1 M D-xylose solution

The above solutions are mixed to prepare a reaction reagent comprising 50 mM or 200 mM D-xylose, 0.068 mM DCPIP, 1.63 mM PMS, 0.1% Triton X-100, and 35 mM PIPES buffer (pH: 6.5).

Measurement Conditions

First, 3 ml of reaction reagent is pre-warmed at 37° C. for 5 minutes. 0.1 ml of GDH solution is added thereto, and the resulting mixture is gently mixed. Then, the change in absorbance at 600 nm is recorded for 5 minutes by a spectrophotometer adjusted at 37° C. with water as a control, and the change in absorbance per minute ($\Delta OD_{TEST}$) is measured from the straight line portion. In a blind test, a solvent that dissolves GDH is added to the reagent mixture, instead of the GDH solution, and the change in absorbance per minute ($\Delta OD_{BLANK}$) is similarly measured. From these values, the reactivity for xylose is determined by the method described in 1 above.

4. Michael is Constant for D-Xylose of Glucose Dehydrogenase

The Michaelis constant (Km) for D-xylose of glucose dehydrogenase is calculated from the Lineweaver-Burk plot in the present invention. Specifically, it can be calculated in such a manner that in the glucose dehydrogenase activity measurement method described in 1 above, the substrate is changed from D-glucose to D-xylose, and the reaction rate is measured at various D-xylose concentrations. The D-xylose concentration used for calculation can be set to an appropriate concentration according to the Michaelis constant of the enzyme. However, in the present invention, when Km is between 0 mM and 100 mM, 4 points are plotted: 30 mM, 50 mM, 100 mM, and 200 mM; when Km is between 100 mM and 500 mM, 4 points are plotted: 50 mM, 200 mM, 600 mM, and 1000 mM; and when Km is between 500 mM and 1500 mM, 4 points are plotted: 50 mM, 200 mM, 600 mM, and 1400 mM.

5. Enzyme Electrode Method

Figure 5:
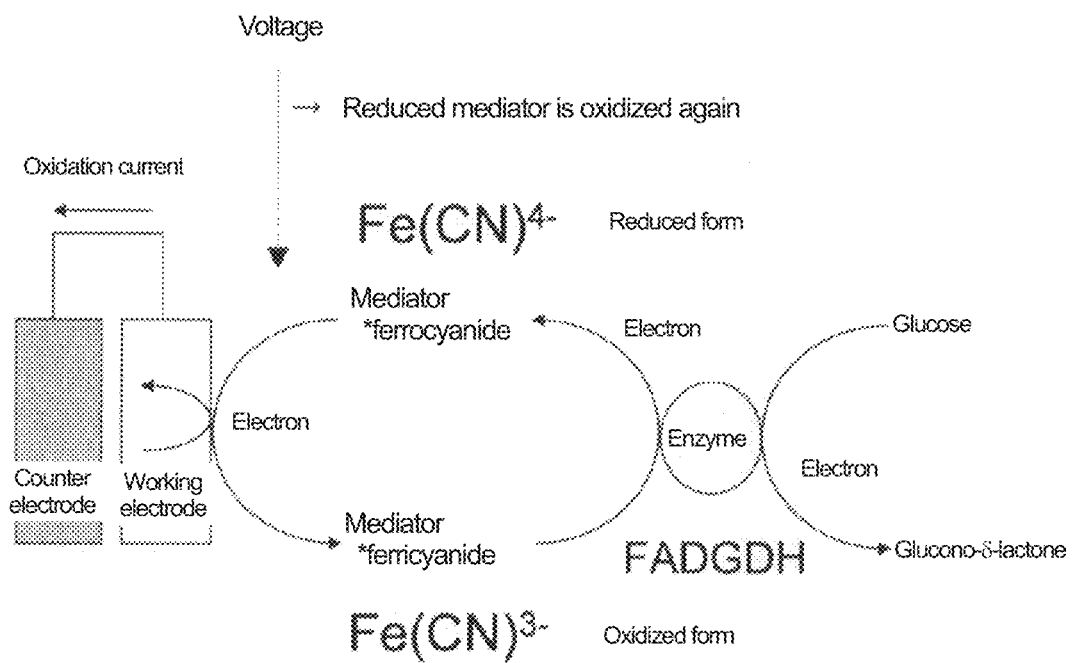
FIG. 5: A diagram showing an example of the principle of a method for measuring D-glucose using an enzyme electrode.

The enzyme electrode method used in the present invention is not particularly limited. FIG. 5 shows an example of the principle of a method for measuring D-glucose using an enzyme electrode. Glucose dehydrogenase catalyzes a reaction that oxidizes the hydroxyl group of glucose to produce glucono-δ-lactone in the presence of a mediator (an electron acceptor). When FADGDH acts on D-glucose, coenzyme FAD becomes FADH2 (reduced form); however, when a ferricyanide (e.g., "$Fe(CN)_6^{3-}$") is present as a mediator, FADH2 (reduced form) converts this into a ferrocyanide (in this case, "$Fe(CN)_6^{4-}$"), and returns itself to FAD (oxidized form). When an electric potential is applied, the ferrocyanide passes an electron to the electrode and returns to a ferricyanide. Therefore, an electrochemical signal can be detected by using such an electron transfer substance as a mediator.

Although the electrochemical measurement method used for the electrode is not particularly limited, various electrochemical measurement methods can be applied by using a general potentiostat or galvanostat. Specific measurement methods include amperometry, potenticmetry, coulometry, and various other methods: however, a method using amperometry to measure a current value generated when a reduced mediator is oxidized by application is particularly preferable. The voltage applied in this case is preferably 10 to 700 mV, more preferably 50 to 500 mV, and even more preferably 100 to 400 mV.

The measurement system may be a two-electrode system or a three-electrode system. The working electrode may be a carbon electrode, or a metal electrode such as platinum, gold, silver, nickel, or palladium. In the case of a carbon electrode, pyrolytic graphite carbon, glassy carbon (GC), carbon paste, plastic formed carbon (PFC), or the like can be used. In the case of a metal electrode, gold is particularly preferable. In general, glucose dehydrogenase is carried on the working electrode. Examples of the method for immobilizing the enzyme on the electrode include a method using a crosslinking reagent, a method in which the enzyme is encapsulated in a polymer matrix, a method in which the enzyme is coated with a dialysis membrane, and a method using a photocrosslinkable polymer, a conductive polymer, and a redox polymer. The enzyme may be carried on a carrier via a functional group and a spacer connecting the functional group and the carrier. Alternatively, the enzyme may be immobilized within a polymer or immobilized on the electrode by adsorption, together with a mediator such as ferricyanide, ferrocene or a derivative thereof, or a combination thereof. As an example of the method, FADGDH is immobilized on a carbon electrode using glutaraldehyde, and then treated with an amine group-containing reagent to block glutaraldehyde. The reference electrode is not particularly limited, and those generally used in electrochemical experiments can be applied. Examples include a saturated calomel electrode and a silver-silver chloride electrode.

The glucose concentration can be measured as follows, for example. First, a buffer is placed in a constant temperature cell and maintained at a constant temperature. As a mediator, potassium ferricyanide, phenazine methosulfate, or the like can be used. An electrode on which FADGDH is immobilized is used as a working electrode, and a counter electrode (e.g., a platinum electrode) and a reference electrode (e.g., an Ag/AgCl electrode) are used. A constant voltage is applied to the carbon electrode, and after the current becomes steady, a sample containing D-glucose is added, and the increase in current is measured. The glucose concentration of the sample can be calculated according to a calibration curve prepared from a D-glucose solution of standard concentration.

Printed electrodes may be used in order to reduce the amount of solution required for measurement, and to simplify the measurement on a small scale. In this case, the electrodes are preferably formed on an insulating substrate. Specifically, the printed electrodes are preferably formed on the substrate by a photolithographic technique, or a printing technique such as screen printing, gravure printing, or flexographic printing. Moreover, examples of the material for the insulating substrate include silicon, glass, ceramic, polyvinyl chloride, polyethylene, polypropylene, polyester, and the like. It is more preferable to use a material that is highly resistant to various solvents and chemicals.

The shape of the electrode is not particularly limited. Examples include a circular shape, an elliptical shape, and a rectangular shape; a circular shape is particularly preferable in terms of easily mounting the enzyme solution to be immobilized. In the case of a circular shape, the radius thereof is preferably 3 mm or less, more preferably 2.5 mm or less, and oven more preferably 2 mm or less. The volume for mounting the enzyme solution is preferably about 1 to 5 µL, and more preferably about 2 to 3 µL. The immobilization reaction after mounting the enzyme solution is preferably performed by leaving it under wet conditions.

The type of solution used for the enzyme reaction is not particularly limited. Examples include phosphate buffers such as PBS, and Good buffers such as TRIS, HOPS, PIPES, HEPES, MES, and TES. The pH of the buffer is preferably about 4.0 to 9.0, more preferably about 5.0 to 8.0, and even more preferably about 6.0 to 7.5. The concentration of the buffer is preferably about 1 to 200 mM, more preferably about 10 to 150 mM, and even more preferably about 20 to 100 mM. Further, various organic acids, salts, preservatives, and like substances can be allowed to coexist as additives, if necessary.

The embodiment of the glucose sensor of the present invention is not particularly limited. For example, a glucose sensor that can mount a chip holding GDH and an electron carrier on an electrode is preferable. The reactive layer formed on the electrode may contain a reaction accelerator, a thickener, a stabilizer, a pH buffer, and other components, in addition to GDH and the electron carrier.

A mediator may be used to mediate the enzyme reaction and the electron transfer between the electrodes. The type of mediator that can be applied is not particularly limited; however, examples include quinones, cytochromes, viologens, phenazines, phenoxazines, phenothiazines, ferricyanides, ferredoxins, ferrocenes, and derivatives thereof. More specific examples include benzoquinone/hydroquinone, ferricyanide/ferrocyanide (potassium or sodium salts), and ferricinium/ferrocene. Phenazine methosulfate, 1-methoxy-5-methylphenazinium methyl sulfate, 2,6-dichlorophenolindophenol, and the like may also be used. Metal complexes of, for example, osmium, cobalt, and ruthenium can also be used. When a compound with a Low water solubility as a mediator and an organic solvent are used, the stability of the enzyme may be lost, or the enzyme activity may be inactivated. To increase the water solubility, the mediator for use may be a compound modified with a hydrophilic polymer such as polyethylene glycol (PEG). The concentration of the mediator in a reaction system is preferably about 1 mM to 1 M, more preferably 5 to 500 mM, and still more preferably 10 to 300 mM. The mediator may also be used by immobilizing it on the electrode together with the enzyme, for example, by using modified products with various functional groups.

The reaction accelerator is not particularly limited, and examples include polyglutamic acid.

The thickener is not particularly limited, as long as it is a substance that can ensure the viscosity required to hold the applied composition on the reactive layer of the glucose sensor. Preferable examples include pullulan, dextran, polyethylene glycol, poly-γ-glutamic acid, carboxymethyl cellulose, polyvinyl pyrrolidone, and clay. Examples of clay include those having a kaolinite structure or a pyrophyllite structure, such as pyrophyllite, mica, smectite, vermlculite, chlorite, kaolinite, and halloysite. Among these, smectite is a preferable example of the thickener. Smectite is further classified into montmorillonite, beidellite, nontronite, saponite, hectorite, and the like. Smectite may be synthetic smectite. For example, commercial products, such as the "Lucentite" series (produced by Coop Chemical Co., Ltd.), are available.

The amount of thickener added to the composition is not particularly limited, as long as the effect of enhancing the stability of the composition is recognized. The concentration thereof in a liquid composition is preferably 0.01% or more and 5% or less, and more preferably 0.1% or more and 1% or less. Further, in a solid composition obtained by heating, freeze drying, or the like, the amount of thickener added is preferably 0.5% or more and 70% or less, and more preferably 4.5% or more and 30% or less.

The stabilizer is not particularly limited, and examples include substances such as glycylglycine, sorbitol, and adonitol. The amount thereof added is not particularly limited, as long as the effect of enhancing the stability of the composition is recognized. The concentration thereof in a liquid composition is preferably 0.1% or more and 10% or less, and more preferably 0.2% or more and 2% or less. Further, in a solid composiiion obtained by heating, freeze drying, or the like, the amount of stabilizer added is preferably 1% or more and 80% or less, and more preferably 2% or more and 50% or less.

When a stabilizer and a thickener are combined, the combination thereof is not particularly limited, but is preferably glycylglycine and carboxymechyl cellulose, glycylglycine and smectite, glycylglycine and polyvinyl pyrrolidone, sorbitol and carboxymethyl cellulose, sorbitol and smectite, sorbitol and polyvinyl pyrrolidone, adonitol and carboxymethyl cellulose, adonitol and smectite, or adonitol and polyvinyl pyrrolidone. Among these combinations, glycylglycine and smectite, sorbitol and smectite, or adonitol and smectite are more preferable.

Although other components are not particularly limited, for example, a surfactant can be used. When a surfactant is used, examples include Triton X-100, Tween 20, sodium deoxycholate, Emulgen 430, and the like.

The composition of the reactive layer may be liquid or dried to solidify. Examples of the solidification method include, but are not limited to, a method of evaporating water by heating, a method of air drying at room temperature or higher, a method of evaporazing water by placing it in vacuum, and a method of removing water by placing it in vacuum in a frozen state.

In the enzyme reaction, in a state in which desired amounts of enzyme and mediator are added and mixed in a desired volume of reaction solution, a predetermined amount of a substrate-containing sample solution, such as blood, is added, and measurement is started at the same time. Although the electrochemical detection method is not particularly limited, it is preferable to measure, as a signal, the change in current that occurs with the transfer of electrons through the mediator as the enzyme reaction proceeds. The sample used for the measurement is not particularly limited, and may be a biological sample such as blood, body fluid, or urine, as well as an aqueous solution containing or possibly containing an enzyme substrate as a component. The measurement may be performed while the reaction temperature is kept constant to the extent possible. Further, it is also possible to develop microanalysis by using a microchannel device or the like.

6. Method for Evaluating D-Xylose Activity in Enzyme Electrode Method

Reactivity for xylose in the enzyme electrode method is evaluated using a sensor chip prepared in the following manner, and using a solution in which a 10 mM glucose solution is spiked with 20 mM (equivalent to 300 mg/dL) D-xylose. This condition is set more severely than the recommended condition of NPL 1 with reference to the condition described in NPL 1.

Production of Sensor Chip

An electrode sensor comprising a working electrode, a counter electrode, and a reference electrode arranged on an insulating substrate is obtained by contract manufacturing from Biodevice Technology Co., Ltd. (Nomi City, Ishikawa Prefecture). In this electrode sensor, the electrodes are printed on the substrate (4.0 m×17 mm). 3 µL of an aqueous solution serving as a reagent layer is mounted on the working electrode (area: about 1.3 $mm^2$) of the sensor. The aqueous solution as the reagent layer has the following formulation:

1000 U/ml FAD-GDH
200 mM potassium ferricyanide
50 mM potassium phosphate buffer (pH: 7.0)

This is dried by heating at 50° C. for 10 minutes to obtain a glucose sensor chip on which 3 U of FADGDH is immobilized per chip.

Measurement Conditions

A 10 mM glucose solution and a solution in which a 10 mM glucose solution is spiked with 20 mM D-xylose are prepared. 5 µL of these sample solutions are dropped by a micropipette on the chip connected to a potentiostat, a voltage of +300 mV is applied 5 seconds after dropping, and the current value is measured. The ratio (%) of a response value to the solution in which a 10 mM glucose solution is spiked with 20 mM D-xylose, with respect to a response value to the 10 mM glucose solution is defined as activity on xylose in the enzyme electrode method. A value of 100% indicates that there is no influence from D-xylose. As this value is further from 100%, there is more positive or negative influence from D-xylose.

The present invention is described in more detail below with reference to Examples; however, the present invention is not limited to these Examples.

EXAMPLES

Example 1: Comparison of Properties of Glucose Dehydrogenase

Four types of FADGDH (GDH1 to GDH4, described later) were compared for their properties. The compared items and the method for measuring each item are as follows.

(a) D-xylose activity in an aqueous system at a substrate concentration of 50 mM
Measurement method: the method described in "3. Method for Evaluating D-Xylose Activity of Glucose Dehydrogenase in Aqueous System"
(b) Michaelis constant (Km) for D-xylose in an aqueous system Measurement method: the method described in "4. Michaelis Constant for D-Xylose of Glucose Dehydrogenase"
(c) Michaelis constant (Km) for D-glucose in an aqueous system Measurement method: the method described in "2. Michaelis Constant for D-Glucose of Glucose Dehydrogenase"
(d) D-xylose activity in an enzyme electrode method Measurement method: the method described in "6. Method for Evaluating D-Xylose Activity in Enzyme Electrode Method"

GDH-1 is obtained by genetically engineering and expressing the DNA sequence of SEQ ID No. 8 of JP527482B using the *Cryptococcus* sp. S-2 D11 strain (PERM SP-11482) described in JP5588578B (the amino acid sequence encoded by SEQ ID No. 8 of JP527482B is SEQ ID No. 1). GDH-2 is obtained by genetically engineering and expressing GDH having an amino acid sequence of SEQ ID No. 2 (the amino acid sequence represented by SEQ ID No. 1 of JP2013-116102A) using the *Cryptococcus* sp. S-2 D11 strain described in JP5588573B (FERM BP-11482).

GDH-3 is obtained by genetically engineering and expressing GDH having an amino acid sequence of SEQ ID No. 3 (the amino acid sequence represented by SEQ ID No. 1 of JP4649993B) using the *Cryptococcus* sp. S-2 D11 strain (FERM BP-11482) described in JP5588578B. GDH-4 is obtained by genetically engineering and expressing GDH having an amino acid sequence of SEQ ID No. 4 (the amino acid sequence represented by SEQ ID No. 1 of JP2015-146773A) using the *Aspergillus oryzae*-NS4 strain (Transformation System for *Aspergillus oryzae* with Double Auxotorophic Mutations, niaD and sC (Bioscience Biotechnology Biochemistry, 1997 Vol. 61, 1367-1369)).

Table 1 shows the results of comparing the various enzyme properties of GDH1 to GDH4.

TABLE 1

|  | GDH-1 | GDH-2 | GDH-3 | GDH-4 |
| --- | --- | --- | --- | --- |
| (a) Xylose activity in 50 mM aqueous system (%) | 11.3 | 1.1 | 1.4 | 2.9 |
| (b) Michaelis constant for xylose (mM) | 39 | 378 | 341 | 82 |
| (c) Michaelis constant for glucose (mM) | 68 | 16 | 31 | 14 |
| (d) Xylose activity in enzyme electrode method (%, spike method) | 190 | 122 | 121 | 180 |

The enzymes listed in Table 1 have a Km for D-glucose of 14 to 82 mM, and their affinity for glucose is sufficiently high. First, the results of GDH-2 and GDH-3 are considered. These two types of GDH had low D-xylose activity in an aqueous system. In particular, when xylose activity (a) in an aqueous system at a substrate concentration of 50 mM was used as an evaluation scale, their xylose activity was 2% or less, and these enzymes were evaluated as being useful. However, when D-xylose activity (d) in an enzyme electrode method was used as an evaluation scale, GDH-2 and GDH-3 both showed values exceeding 120% in the spike method. This suggested a possibility that GDH-2 and GDH-3 had large influence on D-xylose in the glucose measurement by SMBG sensors.

Next, the results of GDH-1 and GDH-4 are considered. D-xylose activity (a) of GDH-4 in the aqueous system is about ¼ the D-xylose activity (a) of GDH-1 in the aqueous system. If D-xylose activity (a) in the aqueous system is an appropriate index for evaluating the influence of GDH, which is used on SMBG sensors, on D-xylose, there should be a significant difference in D-xylose activity (d) in the enzyme electrode method between GDH-1 and GDH-4. However, the difference in D-xylose activity (d) in the enzyme electrode method between GDH-1 and GDH-4 is about 10%, and there is no effect that meets expectations from the difference in their D-xylose activity (a) in the aqueous system.

Here, attention is paid to Km (b) for D-xylose of GDH-1 to 4, and D-xylose activity (d) in the enzyme electrode method. From the comparison between Km (b) for D-xylose of GDH-1 to GDH-4 and D-xylose activity (d) in the enzyme electrode method (FIG. 1), a correlation was expected between Km (b) for D-xylose and D-xylose activity (d) in the enzyme electrode method.

D-xylose activity (d) in the enzyme electrode method decreases depending on Km (b) for D-xylose. A regression line created from Km (b) for D-xylose of GDH-1 to GDH-4 and xylose activity (d) in the enzyme electrode method suggested a possibility that xylose activity (d) in the enzyme electrode method was suppressed when Km (b) for D-xylose was 619 mM or more.

Example 2: Acquisition of GDH-5 and GDH-6, and Property Comparison

In order to verify the above hypothesis derived from the results of Example 1, GDH having a Km (b) for D-xylose of 619 mM or more was searched for. Example 1 of JP2015-84676A describes the construction of a FADGDH random mutant library using *Saccharomyces* yeast as a host. A FADGDH random mutant library was constructed using *Saccharomyces* yeast comprising 1000 strains as a host from DNA encoding GDH having the amino acid sequence of SEQ ID No. 5 by a method based on the method described in Example 1 of JP2015-84676A.

Specifically, random mutations were introduced into FADGDH gene by error-prone PCR using pYESMh6754 (see JP2013-116102A) as a plasmid. On the pYESMh6754, GAL1 promoter and CYC1 terminator are arranged with FADGDH gene between them. Random mutations were introduced using the Diversify PCR Random Mutagenesis Kit (Clontech) according to the protocol attached to the product using primers capable of complementarily binding to the GAL1 promoter and CYC1 terminator. As a result, a DNA fragment containing FADGDH gene having mutations introduced at a certain ratio was obtained. Next, the obtained DNA fragment containing FADGDH gene having mutations introduced at a certain ratio was treated with restriction enzymes KpnI and NotI, and mixed with vector pYES3 (Invitrogen) similarly treated with restriction enzymes KpnI and NotI. Then, a ligation reagent (Toyobo Ligation High) was added in an amount equal to that of the mixed liquid, followed by incubation, thereby carrying out ligation. The thus-ligated DNA was transformed into *Escherichia coli* DH5α competent cells (Competent high DH5α, produced by Toyobo Co., Ltd.) according to the protocol attached to the product to obtain a transformant. The transformant was cultured in an LB medium, and the plasmid was extracted, thereby obtaining a random mutant plasmid library in which mutations were introduced at a constant ratio into FADGDH gene inserted into the plasmid. Subsequently, the random mutant plasmid library was transformed into *Saccharomyces cerevisiae* INVSc1 (Invitrogen). About 2000 grown colonies were used as a FADGDH random mutant library using *Saccharomyces* as a host.

The transformant contained in the library constructed as described above was cultured by a method based on the method described in Example 2 of JP2015-84676A. Specifically, the constructed FADGDH random mutant library using *Saccharomyces* as a host was inoculated in a medium containing 3% yeast extract, 1% polypeptone, and 3% galactose dispensed into each culture cell of ScreenMates (Matrix Technology), and cultured with shaking at 25° C. for 60 hours. Next, the obtained culture solution was centrifuged at 2000 rpm for 15 minutes to obtain a culture supernatant.

Figure 2:
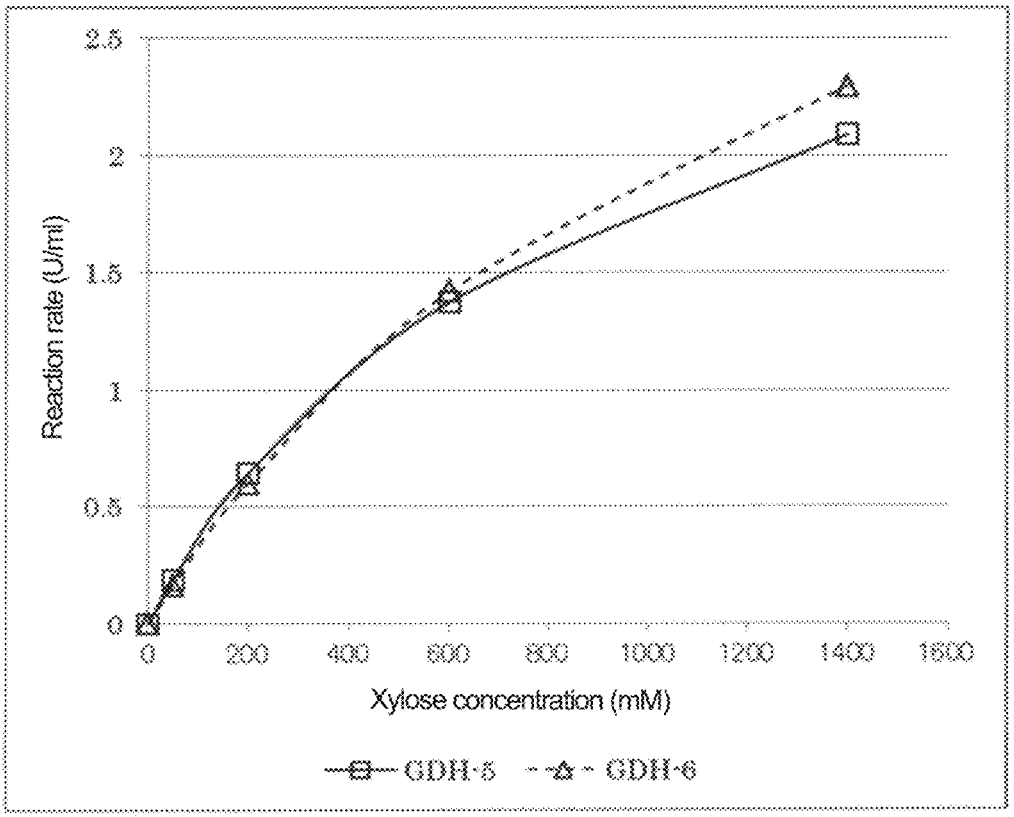
FIG. 2: A graph showing the results of examining the relationship of the reaction rate with respect to the D-xylose concentrations of GDH-5 and GDH-6 in Example 2.
Figure 3:
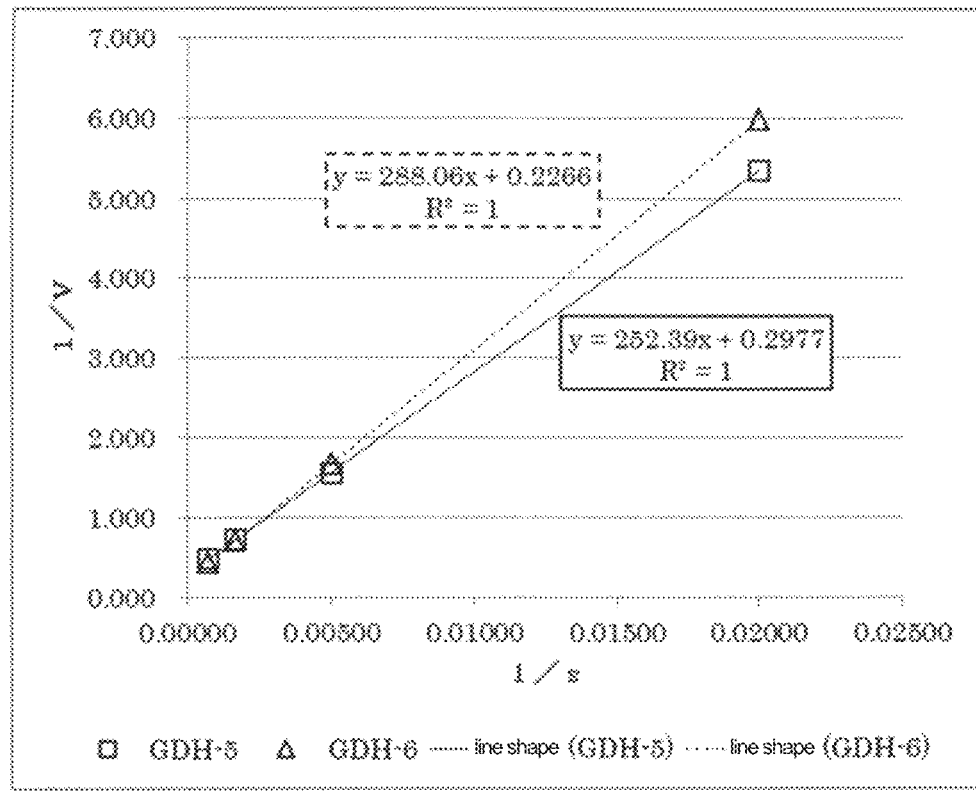
FIG. 3: A graph showing the relationship of the reciprocal of the reaction rate with respect to the reciprocal of the D-xylose concentrations of GDH-5 and GDH-6 (Lineweaver-Burk plot) in Example 2.

From the comparison of activity on D-xylose at concentrations of 200 mM and 600 mM in the culture supernatant, modified GDH that was expected to have a low affinity for D-xylose was selected. The selected modified GDH was purified, and the reaction rate for D-xylose at concentrations of 50 mM, 200 mM, 600 mM, and 1400 mM was confirmed, thereby obtaining GDH-5 with a Km (b) for D-xylose of 819 mM, and GDH-6 with a Km (b) for D-xylose of 1271 mM. FIG. 2 shows the results of examining the relationship of the reaction rate of GDH-5 and GDH-6 for D-xylose at concentrations of 50 mM, 200 mM, 600 mM, and 1400 mM, and FIG. 3 shows the results of Lineweaver-Burk plot, which is the basis for the calculation of Michaelis constant (Km).

For GDH-5 with a Km (b) for D-xylose of 819 mM and GDH-6 with a Km (b) for D-xylose of 1271 mM, D-xylose activity in an aqueous system at a substrate concentration of 200 mM, D-xylose activity (a) in an aqueous system at a substrate concentration of 50 mM, and D-xylose activity (c) in an enzyme electrode method were measured, and compared between GDH1 to GDH4. Table 2 shows the results.

activity (d) in the enzyme electrode method decreases as Km (b) for D-xylose increases. In the region where Km (b) for D-xylose is about 736 mM or more, D-xylose activity (d) in the enzyme electrode method is almost not confirmed, and a state in which D-xylose does not affect the glucose measurement is maintained.

Here, GDH-2 and GDH-5 are compared. In Table 2, GDH-2 and GDH-5 have a D-xylose activity (a) of about 1% in an aqueous system at a substrate concentration of 50 mM. When this point is used as a criterion for evaluation, both are treated as enzymes that are useful in terms of D-xylose activity. However, it was clarified that there was a significant difference in D-xylose activity (d) in the enzyme electrode method between GDH-2 and GDH-5. GDH-2 has a D-xylose activity of 120% in the enzyme electrode method, and there is concern about influence on D-xylose in glucose measurement by SMBG sensors. In contrast, GDH-5 has a D-xylose activity of 100% in the enzyme electrode method, and GDH-5 has less influence on D-xylose in glucose measurement by SMBG sensors.

Thus, it was shown that evaluation of D-xylose activity in an aqueous system alone was not sufficient as physicochemical characteristics for evaluating that GDH used on SMBG sensors had no practical influence on D-xylose. It was found that Km (b) for D-xylose was useful as an alternative index. According to the results of this Example, if Km (b) for D-xylose is 619 mM or more, GDH is considered to have physicochemical characteristics satisfying that it has less practical influence on D-xylose on SMBG sensors.

The reason why such a phenomenon occurs is considered to be as follows.

While the reaction rate of an enzyme in a solution is calculated by observation in minutes, in a sensor system represented by an enzyme electrode method, changes in seconds or milliseconds are observed as current response values. From the results of Example 1, it was assumed that since the instantaneously measured current response value derived from D-xylose degradation was suppressed to be

TABLE 2

|  | GDH-1 | GDH-2 | GDH-3 | GDH-4 | GDH-5 | GDH-6 |
| --- | --- | --- | --- | --- | --- | --- |
| (a) Xylose activity in 50 mM aqueous system (%) | 11.3 | 1.1 | 1.4 | 2.9 | 0.9 | 0.5 |
| (b) Michaelis constant for xylose (mM) | 39 | 378 | 541 | 82 | 819 | 1271 |
| (c) Michaelis constant for glucose (mM) | 68 | 16 | 31 | 14 | 80 | 82 |
| (d) Xylose activity in enzyme electrode method (%, spike method) | 190 | 122 | 121 | 180 | 100 | 101 |

Figure 4:
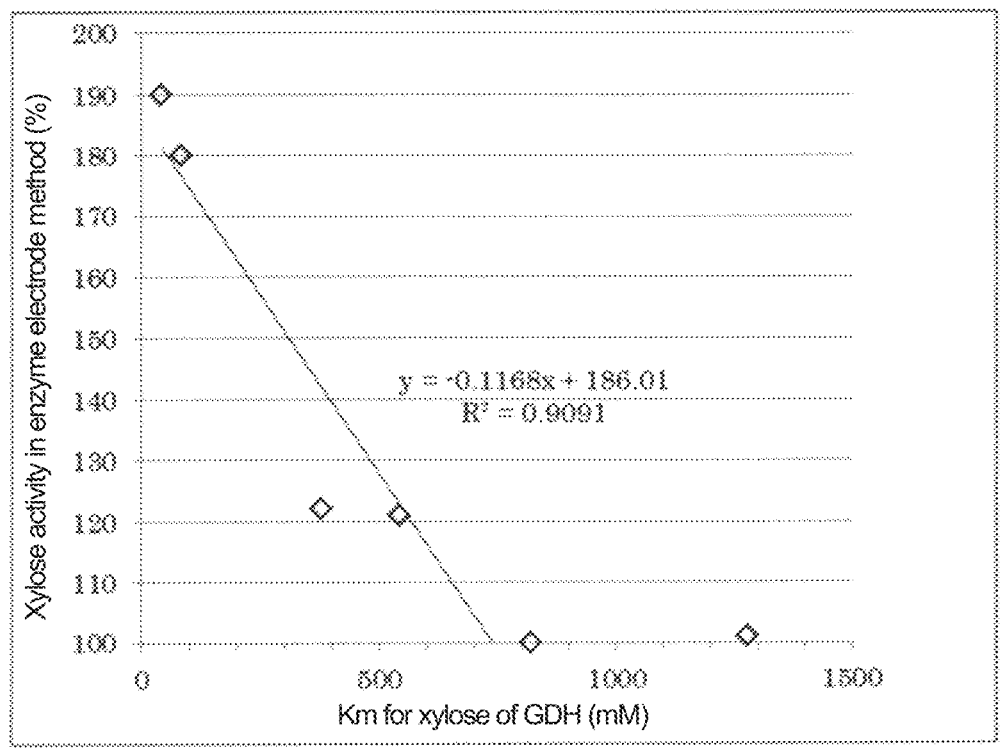
FIG. 4: A graph showing the Michaelis constant (Km) for D-xylose of GDH1 to GDH6, and D-xylose activity in an enzyme electrode method, in Example 2.

As a result, GDH-5 with a Km (b) for D-xylose of 819 mM and GDH-6 with a Km (b) for D-xylose of 1271 mM had a D-xylose activity (c) of 100 to 101% in the enzyme electrode method, and it was confirmed that there was almost no action with D-xylose. FIG. 4 shows a comparison of Km (b) for D-xylose of GDH-1 to GDH-6, and D-xylose activity (c) in the enzyme electrode method.

From the results shown in FIG. 4, in the range where Km (b) for D-xylose is less than about 736 mM, D-xylose low in an enzyme electrode method using an enzyme with a low affinity for D-xylose, i.e., a sufficiently high Km, the variation in the current response values under D-xylose spike conditions would be small.

The D-xylose activity of GDH1 to GDH6 in an aqueous system was also measured at a substrate concentration changed to 200 mM. The results were as follows: GDH-1: 9.9%, GDH-2: 4.9%, GDH-3: 3.6%, GDH-4: 4.6%, GDH-5: 1.8%, and GDH-6: 1.6%.

INDUSTRIAL APPLICABILITY

The present invention makes it possible to provide a glucose monitoring method and a glucose monitoring sensor, both of which are capable of accurate measurement of blood sugar, and are expected to be widely used in accurate control of blood sugar levels in the field of diabetes medical care.

The invention claimed is:

1. A glucose sensor comprising glucose dehydrogenase on a carbon electrode or a metal electrode, the glucose dehydrogenase having (i) a Km for D-xylose of 600 mM or more and 3000 mM or less and (ii) properties (a), (b), or (c):
   (a) a Km for D-glucose of 10 mM or more and 90 mM or less, an optimal temperature of 50° C. to 70° C., a temperature stability of 80% or more as measured by residual activity after treatment at 50° C. for 15 minutes, an optimum pH of 6.5 to 7.5, a pH stability of 2.5 to 10 under treatment conditions at 25° C. for 16 hours, and a sugar content of 10% to 40%,
   (b) a Km for D-glucose of 50 mM or more and 70 mM or less, an optimal temperature of 50° C. to 55° C., a temperature stability of 80% or more as measured by residual activity after treatment at 50° C. for 15 minutes, an optimum pH of about 7, a pH stability of 4 to 8 under treatment conditions at 25° C. for 16 hours, and a sugar content of 20% to 50%, or
   (c) a Km for D-glucose of 5 mM or more and 20 mM or less, an optimal temperature of 45° C. to 50° C., a temperature stability of 80% or more as measured by residual activity after treatment at 45° C. for 15 minutes, an optimum pH of 6 to 6.5, a pH stability of 3.5 to 6.5 under treatment conditions at 25° C. for 16 hours, and a sugar content of 20% to 50%.

2. The glucose sensor according to claim 1, wherein the glucose dehydrogenase further has a D-xylose activity of 95% or more and 105% or less in an enzyme electrode method, where the D-xylose activity is a ratio (%) of a response value to a solution in which a 10 mM D-glucose solution is spiked with 20 mM D-xylose, with respect to a response value to a 10 mM glucose solution.

3. The glucose sensor according to claim 1, further comprising a mediator on the carbon electrode or metal electrode.

4. The glucose sensor according to claim 2, further comprising a mediator on the carbon electrode or metal electrode.

5. A glucose monitoring method using glucose dehydrogenase on a carbon electrode or a metal electrode, the glucose dehydrogenase having (i) a Km for D-xylose of 600 mM or more and 3000 mM or less and (ii) properties (a), (b), or (c):
   (a) a Km for D-glucose of 10 mM or more and 90 mM or less, an optimal temperature of 50° C. to 70° C., a temperature stability of 80% or more as measured by residual activity after treatment at 50° C. for 15 minutes, an optimum pH of 6.5 to 7.5, a pH stability of 2.5 to 10 under treatment conditions at 25° C. for 16 hours, and a sugar content of 10% to 40%,
   (b) a Km for D-glucose of 50 mM or more and 70 mM or less, an optimal temperature of 50° C. to 55° C., a temperature stability of 80% or more as measured by residual activity after treatment at 50 ° C. for 15 minutes, an optimum pH of about 7, a pH stability of 4 to 8 under treatment conditions at 25° C. for 16 hours, and a sugar content of 20% to 50%, or
   (c) a Km for D-glucose of 5 mM or more and 20 mM or less, an optimal temperature of 45° C. to 50° C., a temperature stability of 80% or more as measured by residual activity after treatment at 45 ° C. for 15 minutes, an optimum pH of 6 to 6.5, a pH stability of 3.5 to 6.5 under treatment conditions at 25° C. for 16 hours, and a sugar content of 20% to 50%.

6. The glucose monitoring method according to claim 5, wherein the glucose dehydrogenase has a Km for D-xylose of 619 mM or more and 3000 mM or less.

7. The glucose monitoring method according to claim 6, wherein the glucose dehydrogenase further has a D-xylose activity of 95% or more and 105% or less in an enzyme electrode method, where the D-xylose activity is a ratio (%) of a response value to a solution in which a 10 mM D-glucose solution is spiked with 20 mM D-xylose, with respect to a response value to a 10 mM glucose solution.

8. The glucose monitoring method according to claim 6, wherein an enzyme electrode comprising glucose dehydrogenase is used.

9. The glucose monitoring method according to claim 8, wherein the glucose dehydrogenase further has a D-xylose activity of 95% or more and 105% or less in an enzyme electrode method, where the D-xylose activity is a ratio (%) of a response value to a solution in which a 10 mM D-glucose solution is spiked with 20 mM D-xylose, with respect to a response value to a 10 mM glucose solution.

10. The glucose monitoring method according to claim 5, wherein the glucose dehydrogenase has a Km for D-xylose of 736 mM or more and 3000 mM or less.

11. The glucose monitoring method according to claim 10, wherein the glucose dehydrogenase further has a D-xylose activity of 95% or more and 105% or less in an enzyme electrode method, where the D-xylose activity is a ratio (%) of a response value to a solution in which a 10 mM D-glucose solution is spiked with 20 mM D-xylose, with respect to a response value to a 10 mM glucose solution.

12. The glucose monitoring method according to claim 10, wherein an enzyme electrode comprising glucose dehydrogenase is used.

13. The glucose monitoring method according to claim 12, wherein the glucose dehydrogenase further has a D-xylose activity of 95% or more and 105% or less in an enzyme electrode method, where the D-xylose activity is a ratio (%) of a response value to a solution in which a 10 mM D-glucose solution is spiked with 20 mM D-xylose, with respect to a response value to a 10 mM glucose solution.

14. The glucose monitoring method according to claim 5, wherein an enzyme electrode comprising glucose dehydrogenase is used.

15. The glucose monitoring method according to claim 14, wherein the glucose dehydrogenase further has a D-xylose activity of 95% or more and 105% or less in an enzyme electrode method, where the D-xylose activity is a ratio (%) of a response value to a solution in which a 10 mM D-glucose solution is spiked with 20 mM D-xylose, with respect to a response value to a 10 mM glucose solution.

16. The glucose monitoring method according to claim 5, wherein the glucose dehydrogenase further has a D-xylose activity of 95% or more and 105% or less in an enzyme electrode method, where the D-xylose activity is a ratio (%) of a response value to a solution in which a 10 mM D-glucose solution is spiked with 20 mM D-xylose, with respect to a response value to a 10 mM glucose solution.

17. A method for producing the glucose sensor according to claim 1, comprising
   measuring the Michaelis constant (Km) of glucose dehydrogenase for D-xylose,
   selecting glucose dehydrogenase having (i) a Km for D-xylose of 600 mM or more and 3000 mM or less and (ii) properties (a), (b), or (c):
   (a) a Km for D-glucose of 10 mM or more and 90 mM or less, an optimal temperature of 50° C. to 70° C., a temperature stability of 80% or more as measured by residual activity after treatment at 50° C. for 15 minutes, an optimum pH of 6.5 to 7.5, a pH stability of 2.5 to 10 under treatment conditions at 25° C. for 16 hours, and a sugar content of 10% to 40%, (b) a Km for D-glucose of 50 mM or more and 70 mM or less, an optimal temperature of 50° C. to 55° C., a temperature stability of 80% or more as measured by residual activity after treatment at 50° C. for 15 minutes, an optimum pH of about 7, a pH stability of 4 to 8 under treatment conditions at 25° C. for 16 hours, and a sugar content of 20% to 50%, or (c) a Km for D-glucose of 5 mM or more and 20 mM or less, an optimal temperature of 45° C. to 50° C., a temperature stability of 80% or more as measured by residual activity after treatment at 45° C. for 15 minutes, an optimum pH of 6 to 6.5, a pH stability of 3.5 to 6.5 under treatment conditions at 25° C. for 16 hours, and a sugar content of 20% to 50%, and immobilizing the selected glucose dehydrogenase on a carbon electrode or a metal electrode.

* * * * *

```
                         SEQUENCE LISTING

<160> NUMBER OF SEQ ID NOS: 5

<210> SEQ ID NO 1
<211> LENGTH: 572
<212> TYPE: PRT
<213> ORGANISM: Aspergillus oryzae

<400> SEQUENCE: 1

Met Lys Asn Thr Thr Thr Tyr Asp Tyr Ile Val Val Gly Gly Gly Thr
1               5                   10                  15

Ser Gly Leu Val Val Ala Asn Arg Leu Ser Glu Asn Pro Asp Val Ser
                20                  25                  30

Val Leu Leu Leu Glu Ala Gly Ala Ser Val Phe Asn Asn Pro Asp Val
            35                  40                  45

Thr Asn Ala Asn Gly Tyr Gly Leu Ala Phe Gly Ser Ala Ile Asp Trp
    50                  55                  60

Gln Tyr Gln Ser Ile Asn Gln Ser Tyr Ala Gly Gly Lys Gln Gln Val
65                  70                  75                  80

Leu Arg Ala Gly Lys Ala Leu Gly Gly Thr Ser Thr Ile Asn Gly Met
                85                  90                  95

Ala Tyr Thr Arg Ala Glu Asp Val Gln Ile Asp Val Trp Gln Lys Leu
            100                 105                 110

Gly Asn Glu Gly Trp Thr Trp Lys Asp Leu Leu Pro Tyr Tyr Leu Lys
        115                 120                 125

Ser Glu Asn Leu Thr Ala Pro Thr Ser Ser Gln Val Ala Ala Gly Ala
    130                 135                 140

Ala Tyr Asn Pro Ala Val Asn Gly Lys Glu Gly Pro Leu Lys Val Gly
145                 150                 155                 160

Trp Ser Gly Ser Leu Ala Ser Gly Asn Leu Ser Val Ala Leu Asn Arg
                165                 170                 175

Thr Phe Gln Ala Ala Gly Val Pro Trp Val Glu Asp Val Asn Gly Gly
            180                 185                 190

Lys Met Arg Gly Phe Asn Ile Tyr Pro Ser Thr Leu Asp Val Asp Leu
        195                 200                 205

Asn Val Arg Glu Asp Ala Ala Arg Ala Tyr Tyr Phe Pro Tyr Asp Asp
    210                 215                 220

Arg Lys Asn Leu His Leu Leu Glu Asn Thr Thr Ala Asn Arg Leu Phe
225                 230                 235                 240

Trp Lys Asn Gly Ser Ala Glu Glu Ala Ile Ala Asp Gly Val Glu Ile
                245                 250                 255

Thr Ser Ala Asp Gly Lys Val Thr Arg Val His Ala Lys Lys Glu Val
            260                 265                 270

Ile Ile Ser Ala Gly Ala Leu Arg Ser Pro Leu Ile Leu Glu Leu Ser
        275                 280                 285

Gly Val Gly Asn Pro Thr Ile Leu Lys Lys Asn Asn Ile Thr Pro Arg
    290                 295                 300

Val Asp Leu Pro Thr Val Gly Glu Asn Leu Gln Asp Gln Phe Asn Asn
305                 310                 315                 320

Gly Met Ala Gly Glu Gly Tyr Gly Val Leu Ala Gly Ala Ser Thr Val
                325                 330                 335
```

```
Thr Tyr Pro Ser Ile Ser Asp Val Phe Gly Asn Glu Thr Asp Ser Ile
                340                 345                 350

Val Ala Ser Leu Arg Ser Gln Leu Ser Asp Tyr Ala Ala Ala Thr Val
            355                 360                 365

Lys Val Ser Asn Gly His Met Lys Gln Glu Asp Leu Glu Arg Leu Tyr
        370                 375                 380

Gln Leu Gln Phe Asp Leu Ile Val Lys Asp Lys Val Pro Ile Ala Glu
385                 390                 395                 400

Ile Leu Phe His Pro Gly Gly Gly Asn Ala Val Ser Ser Glu Phe Trp
                405                 410                 415

Gly Leu Leu Pro Phe Ala Arg Gly Asn Ile His Ile Ser Ser Asn Asp
            420                 425                 430

Pro Thr Ala Pro Ala Ala Ile Asn Pro Asn Tyr Phe Met Phe Glu Trp
        435                 440                 445

Asp Gly Lys Ser Gln Ala Gly Ile Ala Lys Tyr Ile Arg Lys Ile Leu
        450                 455                 460

Arg Ser Ala Pro Leu Asn Lys Leu Ile Ala Lys Glu Thr Lys Pro Gly
465                 470                 475                 480

Leu Ser Glu Ile Pro Ala Thr Ala Ala Asp Glu Lys Trp Val Glu Trp
                485                 490                 495

Leu Lys Ala Asn Tyr Arg Ser Asn Phe His Pro Val Gly Thr Ala Ala
            500                 505                 510

Met Met Pro Arg Ser Ile Gly Val Val Asp Asn Leu Arg Val
        515                 520                 525

Tyr Gly Thr Ser Asn Val Arg Val Val Asp Ala Ser Val Leu Pro Phe
        530                 535                 540

Gln Val Cys Gly His Leu Val Ser Thr Leu Tyr Ala Val Ala Glu Arg
545                 550                 555                 560

Ala Ser Asp Leu Ile Lys Glu Asp Ala Lys Ser Ala
                565                 570

<210> SEQ ID NO 2
<211> LENGTH: 635
<212> TYPE: PRT
<213> ORGANISM: Mucor hiemalis

<400> SEQUENCE: 2

Met Lys Ile Ser Val Ala Ile Val Thr Ile Ala Ala Phe Ala Ser
1               5                   10                  15

Phe Ala Asn Ala Gln Lys Thr Thr Ser Asn Thr Tyr Asp Tyr Val
            20                  25                  30

Ile Val Gly Gly Gly Val Gly Gly Leu Ala Leu Ala Ser Arg Leu Ser
        35                  40                  45

Glu Asp Lys Ser Val Thr Val Ala Val Leu Glu Gly Pro Asn Ala
        50                  55                  60

Asp Glu Gln Phe Val Val Tyr Ala Pro Gly Met Tyr Gly Gln Ala Val
65                  70                  75                  80

Gly Thr Asp Leu Cys Pro Leu Arg Pro Thr Val Pro Gln Glu Ala Met
            85                  90                  95

Asn Asn Arg Thr Leu Thr Ile Ala Thr Gly Lys Leu Leu Gly Gly Gly
            100                 105                 110

Ser Ala Ile Asn Gly Leu Val Trp Thr Arg Gly Ala Leu Lys Asp Phe
        115                 120                 125

Asp Ala Trp Glu Glu Leu Gly Asn Pro Gly Trp Asn Gly Arg Thr Met
        130                 135                 140
```

-continued

```
Phe Lys Tyr Phe Lys Lys Val Glu Arg Phe His Pro Pro Thr Lys Ala
145                 150                 155                 160

Gln Val Gln Tyr Gly Ala Thr Tyr Gln Lys Gly Val His Gly Lys Asn
                165                 170                 175

Gly Arg Ile Asp Ile Ser Phe Pro Glu Phe Gln Phe Pro Gln Ser Ala
            180                 185                 190

Asn Trp Asn Ala Ser Leu Ala Thr Leu Asp Phe Thr His Gln Gln Asp
        195                 200                 205

Leu Leu Asn Gly Ser Leu His Gly Tyr Ser Thr Thr Pro Asn Thr Leu
210                 215                 220

Asp Pro Lys Thr Ala Arg Arg Val Asp Ser Tyr Thr Gly Tyr Ile Ala
225                 230                 235                 240

Pro Phe Val Ser Arg Lys Asn Leu Phe Val Leu Ala Asn His Thr Val
                245                 250                 255

Ser Arg Ile Gln Phe Lys Pro Lys Asn Gly Thr Glu Leu Leu Lys Ala
            260                 265                 270

Val Gly Val Glu Trp Tyr Thr Thr Gly Asp Asn Ser Asn Lys Gln Thr
        275                 280                 285

Ile Lys Ala Arg Arg Glu Val Ile Val Ser Ser Gly Ser Ile Gly Ser
290                 295                 300

Pro Lys Leu Leu Glu Ile Ser Gly Ile Gly Asn Lys Asp Ile Val Thr
305                 310                 315                 320

Ala Ala Gly Val Gln Ser Leu Ile Asp Leu Pro Gly Val Gly Ser Asn
                325                 330                 335

Met Gln Asp His Val His Ala Val Thr Val Ser Thr Thr Asn Ile Thr
            340                 345                 350

Gly Phe Thr Thr Asp Ser Val Phe Gln Asn Glu Thr Leu Ala Glu Glu
        355                 360                 365

Gln Arg Gln Gln Tyr Tyr Asn Asn Lys Thr Gly Ile Trp Thr Thr Thr
370                 375                 380

Pro Asn Asn Leu Gly Tyr Pro Ser Pro Ser Gln Leu Phe Asp Gly Thr
385                 390                 395                 400

Ser Phe Glu Ser Gly Gln Ala Phe Ala Asn Arg Ile Arg Asn Ser Thr
                405                 410                 415

Asp Gln Trp Ala Glu Tyr Tyr Ala Ser Thr Asn Ala Thr Asn Ile Glu
            420                 425                 430

Leu Leu Lys Lys Gln Tyr Ala Ile Val Ala Ser Arg Tyr Glu Glu Asn
        435                 440                 445

Tyr Leu Ser Pro Ile Glu Ile Asn Phe Thr Pro Gly Tyr Gly Gly Thr
450                 455                 460

Thr Asp Val Asp Leu Lys Asn Asn Lys Tyr Gln Thr Val Asn His Val
465                 470                 475                 480

Leu Ile Ala Pro Leu Ser Arg Gly Tyr Thr His Ile Asn Ser Ser Asn
                485                 490                 495

Ile Glu Asp Pro Val Val Ile Asn Pro Gln Tyr Tyr Thr His Pro Met
            500                 505                 510

Asp Val Asp Val His Ile Ala Ser Thr Lys Leu Ala Arg Arg Ile Leu
        515                 520                 525

Gly Ala Glu Pro Gly Leu Ala Ser Ile Asn Ser Gly Glu Ile Gln Pro
530                 535                 540

Gly Ser Asn Ile Thr Ser Asp Glu Asp Val Lys Gln Trp Leu Ala Asp
545                 550                 555                 560
```

-continued

```
Asn Val Arg Ser Asp Trp His Pro Val Gly Thr Cys Ala Met Leu Pro
            565                 570                 575

Arg Glu Leu Gly Gly Val Val Asp Pro Asn Leu Leu Val Tyr Gly Thr
        580                 585                 590

Ala Asn Leu Arg Val Val Asp Ala Ser Ile Met Pro Leu Glu Ile Ser
        595                 600                 605

Ser His Leu Met Gln Pro Thr Tyr Gly Val Ala Glu Lys Ala Ala Asp
610                 615                 620

Ile Ile Lys Met Ser Arg Lys Asn Asn Asn
625                 630                 635

<210> SEQ ID NO 3
<211> LENGTH: 641
<212> TYPE: PRT
<213> ORGANISM: Mucor prainii

<400> SEQUENCE: 3

Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser Ser Thr Asp Thr Tyr
            20                  25                  30

Asp Tyr Val Thr Val Gly Gly Gly Val Ala Gly Leu Ala Leu Ala Ser
        35                  40                  45

Arg Ile Ser Glu Asn Lys Asp Val Thr Val Ala Val Leu Glu Ser Gly
    50                  55                  60

Pro Asn Ala Asn Asp Arg Phe Val Val Tyr Ala Pro Gly Met Tyr Gly
65                  70                  75                  80

Gln Ala Val Gly Thr Asp Leu Cys Pro Leu Ile Pro Thr Thr Pro Gln
                85                  90                  95

Glu Asn Met Gly Asn Arg Ser Leu Thr Ile Ala Thr Gly Arg Leu Leu
            100                 105                 110

Gly Gly Gly Ser Ala Ile Asn Gly Leu Val Trp Thr Arg Gly Gly Leu
        115                 120                 125

Lys Asp Tyr Asp Ala Trp Glu Glu Leu Gly Asn Pro Gly Trp Asn Gly
    130                 135                 140

Ala Asn Leu Phe Lys Tyr Phe Lys Lys Val Glu Asn Phe Thr Pro Pro
145                 150                 155                 160

Thr Pro Ala Gln Ile Glu Tyr Gly Ala Thr Tyr Gln Lys Ser Ala His
                165                 170                 175

Gly Lys Lys Gly Pro Ile Asp Val Ser Phe Thr Asn Tyr Glu Phe Ser
            180                 185                 190

Gln Ser Ala Ser Trp Asn Ala Ser Leu Glu Thr Leu Asp Phe Thr Ala
        195                 200                 205

Leu Pro Asp Ile Leu Asn Gly Thr Leu Ala Gly Tyr Ser Thr Thr Pro
    210                 215                 220

Asn Ile Leu Asp Pro Glu Thr Val Gln Arg Val Asp Ser Tyr Thr Gly
225                 230                 235                 240

Tyr Ile Ala Pro Tyr Thr Ser Arg Asn Asn Leu Asn Val Leu Ala Asn
                245                 250                 255

His Thr Val Ser Arg Ile Gln Phe Ala Pro Lys Asn Gly Ser Glu Pro
            260                 265                 270

Leu Lys Ala Thr Gly Val Glu Trp Tyr Pro Thr Gly Asn Lys Asn Gln
        275                 280                 285

Lys Gln Ile Ile Lys Ala Arg Tyr Glu Val Ile Ile Ser Ser Gly Ala
    290                 295                 300
```

```
Ile Gly Ser Pro Lys Leu Leu Glu Ile Ser Gly Ile Gly Asn Lys Asp
305                 310                 315                 320

Ile Val Ser Ala Ala Gly Val Glu Ser Leu Ile Asp Leu Pro Gly Val
            325                 330                 335

Gly Ser Asn Met Gln Asp His Val His Ala Ile Thr Val Ser Thr Thr
        340                 345                 350

Asn Ile Thr Gly Tyr Thr Thr Asn Ser Val Phe Val Asn Glu Thr Leu
    355                 360                 365

Ala Gln Glu Gln Arg Glu Gly Tyr Glu Ala Asn Lys Thr Gly Ile Trp
370                 375                 380

Ala Thr Thr Pro Asn Asn Leu Gly Tyr Pro Thr Pro Glu Gln Leu Phe
385                 390                 395                 400

Asn Gly Thr Glu Phe Val Ser Gly Lys Glu Phe Ala Asp Lys Ile Arg
            405                 410                 415

Asn Ser Thr Asp Glu Trp Ala Asn Tyr Ala Ser Thr Asn Ala Ser
        420                 425                 430

Asn Val Glu Leu Leu Lys Lys Gln Tyr Ala Ile Val Ala Ser Arg Tyr
    435                 440                 445

Glu Glu Asn Tyr Leu Ser Pro Ile Glu Ile Asn Phe Thr Pro Gly Tyr
450                 455                 460

Glu Gly Ser Gly Asn Val Asp Leu Gln Asn Asn Lys Tyr Gln Thr Val
465                 470                 475                 480

Asn His Val Leu Ile Ala Pro Leu Ser Arg Gly Tyr Thr His Ile Asn
            485                 490                 495

Ser Ser Asp Val Glu Asp His Ser Val Ile Asn Pro Gln Tyr Tyr Ser
        500                 505                 510

His Pro Met Asp Ile Asp Val His Ile Ala Ser Thr Lys Leu Ala Arg
    515                 520                 525

Glu Ile Ile Thr Ala Ser Pro Gly Leu Gly Asp Ile Asn Ser Gly Glu
530                 535                 540

Ile Glu Pro Gly Met Asn Ile Thr Ser Glu Asp Asp Leu Arg Ser Trp
545                 550                 555                 560

Leu Ser Asn Asn Val Arg Ser Asp Trp His Pro Val Gly Thr Cys Ala
            565                 570                 575

Met Leu Pro Lys Glu Leu Gly Gly Val Val Ser Pro Ala Leu Met Val
        580                 585                 590

Tyr Gly Thr Ser Asn Leu Arg Val Val Asp Ala Ser Ile Met Pro Leu
    595                 600                 605

Glu Val Ser Ser His Leu Met Gln Pro Thr Tyr Gly Ile Ala Glu Lys
610                 615                 620

Ala Ala Asp Ile Ile Lys Asn Phe Tyr Lys Thr Gln His Lys Asn Gln
625                 630                 635                 640

Asn

<210> SEQ ID NO 4
<211> LENGTH: 593
<212> TYPE: PRT
<213> ORGANISM: Taralomyces sp.

<400> SEQUENCE: 4

Met Leu Leu Pro Ser Leu Ala Leu Ala Ala Phe Ser Val Gly Ala Ala
1               5                   10                  15

Ala Lys Ser His His Ser Gly Ser Ser Ser Ser Tyr His Tyr Asp
            20                  25                  30
```

```
Tyr Val Ile Val Gly Gly Thr Ser Gly Leu Val Ala Asn Arg
        35                  40                  45

Leu Ser Glu Leu His Asp Val Thr Ala Val Ile Glu Ala Gly Asp
50                  55                  60

Ser Ala Leu Asn Phe Asn Val Ser Asn Val Met Gly Tyr Ser Thr
65                  70                  75                  80

Ala Phe Gly Thr Gln Val Asp Trp Ala Tyr Arg Thr Glu Asn Gln Thr
                85                  90                  95

Tyr Ala Gly Gly Leu Gln Gln Thr Ile Arg Ala Gly Lys Ala Leu Gly
                100                 105                 110

Gly Thr Ser Thr Ile Asn Gly Met Ser Tyr Thr Arg Ala Glu Asp Val
                115                 120                 125

Gln Ile Asp Ile Trp Glu Val Gly Asn Lys Gly Trp Asn Trp Thr
130                 135                 140

Asn Leu Leu Pro Tyr Tyr Lys Lys Ser Glu Gly Phe Gln Val Pro Thr
145                 150                 155                 160

Gln Asp Gln Ile Ala His Gly Ala Asn Tyr Asn Ala Ser Tyr His Gly
                165                 170                 175

Leu Asp Gly Pro Leu Lys Val Gly Trp Pro Thr Ser Met Thr Asn Ser
                180                 185                 190

Ser Val Phe Tyr Ala Leu Lys Gln Thr Phe Glu Asn Leu Gly Val Asp
                195                 200                 205

Tyr Asn Pro Asp Ser Ala Gly Gly Lys Met Val Gly Phe Thr Asp His
                210                 215                 220

Pro Asp Thr Leu Asp Arg Ala Lys Asn Val Arg Glu Asp Ala Ala Arg
225                 230                 235                 240

Ala Tyr Tyr Trp Pro Tyr Glu Ala Arg Ser Asn Leu Lys Ile Ile Ser
                245                 250                 255

Asn Thr Arg Ala Asn Arg Val Val Trp Ala Asn Ser Thr Arg Gly Gly
                260                 265                 270

Glu Ala Val Ala Val Gly Val Glu Val Thr Asn Glu Tyr Gly Thr Glu
                275                 280                 285

Thr Ile Tyr Ala Asp Arg Glu Val Val Leu Ser Ala Gly Ala Leu Arg
                290                 295                 300

Ser Pro Ala Leu Leu Glu Leu Ser Gly Val Gly Asn Pro Ala Val Leu
305                 310                 315                 320

Gly Gln His Gly Ile Pro Val Arg Val Asn Leu Thr Val Gly Glu
                325                 330                 335

Asn Leu Gln Asp Gln Thr Asn Asn Gly Leu Ser Trp Ala Gly Thr Asp
                340                 345                 350

Thr Leu Thr Gly Leu Ala Ala Phe Ser Ala Leu Pro Ser Val Asn Gln
                355                 360                 365

Leu Tyr Gly Asp Asn Ala Ala Asp Leu Ala Ala Ser Val Lys Ser Gln
                370                 375                 380

Leu Ala Ser Tyr Ala Gln Thr Val Ala Gln Ala Ser Lys Gly Ala Leu
385                 390                 395                 400

Arg Glu Ala Asp Leu Leu Asp Ala Phe Thr Leu Gln Tyr Asp Leu Ile
                405                 410                 415

Phe Lys Ser Gln Val Pro Phe Thr Glu Ile Val Phe Ala Pro Ser Ser
                420                 425                 430

Gln Ser Phe Ala Val Glu Tyr Trp Pro Leu Leu Pro Phe Ser Arg Gly
                435                 440                 445
```

```
Ser Val His Ile Arg Ser Ala Asn Ala Ser Asp Leu Pro Ala Ile Asn
    450                 455                 460

Pro Asn Tyr Phe Met Phe Ala Gln Asp Ala Glu Ala Gln Val Thr Val
465                 470                 475                 480

Ala Lys Tyr Ile Arg Lys Ala Leu Ala Thr Ala Pro Leu Ser Gly Leu
                485                 490                 495

Val Asp Lys Glu Leu Ser Pro Gly Leu Gly Ala Leu Pro Ala Asn Ala
            500                 505                 510

Ser Ser Ser Thr Trp Asp Ser Trp Ile Lys Ala Asn Tyr Arg Thr Asn
        515                 520                 525

Tyr His Pro Val Gly Thr Ala Ile Met Leu Pro Arg Glu Lys Gly Gly
    530                 535                 540

Val Val Ser Pro Glu Leu Lys Val Tyr Gly Thr Lys Asn Leu Arg Val
545                 550                 555                 560

Val Asp Ala Ser Val Leu Pro Phe Gln Leu Cys Gly His Leu Thr Ser
                565                 570                 575

Thr Leu Tyr Ala Val Ala Glu Arg Ala Ser Asp Leu Ile Lys Glu Ser
            580                 585                 590

His

<210> SEQ ID NO 5
<211> LENGTH: 635
<212> TYPE: PRT
<213> ORGANISM: Mucor hiemalis NBRC6754

<400> SEQUENCE: 5

Met Lys Ile Ser Val Ala Ile Val Thr Ile Ala Ala Ala Phe Ala Ser
1               5                   10                  15

Phe Ala Asn Ala Gln Lys Thr Thr Ser Asn Thr Tyr Asp Tyr Val
            20                  25                  30

Ile Val Gly Gly Gly Val Gly Gly Leu Ala Leu Ala Ser Arg Leu Ser
            35                  40                  45

Glu Asp Lys Ser Val Thr Val Ala Val Leu Glu Ala Gly Pro Asn Ala
    50                  55                  60

Asp Glu Gln Phe Val Val Tyr Ala Pro Gly Met Tyr Gly Gln Ala Val
65                  70                  75                  80

Gly Thr Asp Leu Cys Pro Leu Arg Pro Thr Val Pro Gln Glu Ala Met
                85                  90                  95

Asn Asn Arg Thr Leu Thr Ile Ala Thr Gly Lys Leu Leu Gly Gly Gly
            100                 105                 110

Ser Ala Ile Asn Gly Leu Val Trp Thr Arg Gly Ala Leu Lys Asp Phe
        115                 120                 125

Asp Ala Trp Glu Glu Leu Gly Asn Pro Gly Trp Asn Gly Arg Thr Met
130                 135                 140

Phe Lys Tyr Phe Lys Lys Val Glu Arg Phe His Pro Pro Thr Lys Ala
145                 150                 155                 160

Gln Val Gln Tyr Gly Ala Thr Tyr Gln Lys Gly Val His Gly Lys Asn
                165                 170                 175

Gly Arg Ile Asp Ile Ser Phe Pro Glu Phe Gln Phe Pro Gln Ser Ala
            180                 185                 190

Asn Trp Asn Ala Ser Leu Ala Thr Leu Asp Phe Thr His Gln Gln Asp
        195                 200                 205

Leu Leu Asn Gly Ser Leu His Gly Tyr Ser Thr Thr Pro Asn Thr Leu
    210                 215                 220
```

-continued

Asp Pro Lys Thr Ala Arg Arg Val Asp Ser Tyr Thr Gly Tyr Ile Ala
225                 230                 235                 240

Pro Phe Val Ser Arg Lys Asn Leu Phe Val Leu Ala Asn His Thr Val
            245                 250                 255

Ser Arg Ile Gln Phe Lys Pro Lys Asn Gly Thr Glu Leu Leu Lys Ala
        260                 265                 270

Val Gly Val Glu Trp Tyr Thr Thr Gly Asp Asn Ser Asn Lys Gln Thr
    275                 280                 285

Ile Lys Ala Arg Arg Glu Val Ile Val Ser Ser Gly Ser Ile Gly Ser
290                 295                 300

Pro Lys Leu Leu Glu Ile Ser Gly Ile Gly Asn Lys Asp Ile Val Thr
305                 310                 315                 320

Ala Ala Gly Val Gln Ser Leu Ile Asp Leu Pro Gly Val Gly Ser Asn
            325                 330                 335

Met Gln Asp His Val His Ala Val Thr Val Ser Thr Thr Asn Ile Thr
        340                 345                 350

Gly Phe Thr Thr Asp Ser Val Phe Gln Asn Glu Thr Leu Ala Glu Glu
    355                 360                 365

Gln Arg Gln Gln Tyr Tyr Asn Asn Lys Thr Gly Ile Trp Thr Thr Thr
370                 375                 380

Pro Asn Asn Leu Gly Tyr Pro Ser Pro Ser Gln Leu Phe Asp Gly Thr
385                 390                 395                 400

Ser Phe Glu Ser Gly Gln Ala Phe Ala Asn Arg Ile Arg Asn Ser Thr
            405                 410                 415

Asp Gln Trp Ala Glu Tyr Tyr Ala Ser Thr Asn Ala Thr Asn Ile Glu
        420                 425                 430

Leu Leu Lys Lys Gln Tyr Ala Ile Val Ala Ser Arg Tyr Glu Glu Asn
    435                 440                 445

Tyr Leu Ser Pro Ile Glu Ile Asn Phe Thr Pro Gly Tyr Gly Gly Thr
450                 455                 460

Thr Asp Val Asp Leu Lys Asn Asn Lys Tyr Gln Thr Val Asn His Val
465                 470                 475                 480

Leu Ile Ala Pro Leu Ser Arg Gly Tyr Thr His Ile Asn Ser Ser Asn
            485                 490                 495

Ile Glu Asp Pro Val Val Ile Asn Pro Gln Tyr Tyr Thr His Pro Met
        500                 505                 510

Asp Val Asp Val His Ile Ala Ser Thr Lys Leu Ala Arg Arg Ile Leu
    515                 520                 525

Gly Ala Glu Pro Gly Leu Ala Ser Ile Asn Ser Gly Glu Ile Gln Pro
530                 535                 540

Gly Ser Asn Ile Thr Ser Asp Glu Asp Val Lys Gln Trp Leu Ala Asp
545                 550                 555                 560

Asn Val Arg Ser Asp Trp His Pro Val Gly Thr Cys Ala Met Leu Pro
            565                 570                 575

Arg Glu Leu Gly Gly Val Val Asp Pro Asn Leu Leu Val Tyr Gly Thr
        580                 585                 590

Ala Asn Leu Arg Val Val Asp Ala Ser Ile Met Pro Leu Glu Ile Ser
    595                 600                 605

Ser His Leu Met Gln Pro Thr Tyr Gly Val Ala Glu Lys Ala Ala Asp
610                 615                 620

Ile Ile Lys Met Ser Arg Lys Asn Asn Asn
625                 630                 635